(12) United States Patent
Voigt et al.

(10) Patent No.: US 10,109,049 B2
(45) Date of Patent: Oct. 23, 2018

(54) METHOD OF SCAN GEOMETRY PLANNING FOR DETERMINING WALL THICKNESS OF AN ANATOMIC DETAIL USING MAGNETIC RESONANCE IMAGING

(71) Applicant: KONINKLIJKE PHILIPS N.V., Eindhoven (NL)

(72) Inventors: Tobias Ratko Voigt, Eindhoven (NL); Steffen Weiss, Eindhoven (NL); Sascha Krueger, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 15/125,602

(22) PCT Filed: Mar. 9, 2015

(86) PCT No.: PCT/EP2015/054798
§ 371 (c)(1),
(2) Date: Sep. 13, 2016

(87) PCT Pub. No.: WO2015/139977
PCT Pub. Date: Sep. 24, 2015

(65) Prior Publication Data
US 2017/0004618 A1 Jan. 5, 2017

(30) Foreign Application Priority Data

Mar. 19, 2014 (EP) .................................. 14160641

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/1072* (2013.01);
(Continued)

(58) Field of Classification Search
None
See application file for complete search history.

(56) References Cited

U.S. PATENT DOCUMENTS 5,601,084 A * 2/1997 Sheehan ................ B82Y 15/00
600/450
7,966,055 B2 6/2011 Guehring et al.
(Continued)

OTHER PUBLICATIONS

Koken et al "Atrial Thickness Mapping for EP Ablation Using Black-Blood Restricted Field of View MRI" Proc. Intl. Soc. Mag. Reson. Med. 19 (2011) p. 3734.
(Continued)

*Primary Examiner* — Idowu O Osifade

(57) ABSTRACT

A method for determining wall thickness of an anatomic detail (52), in particular of the heart, of a subject of interest (20) by magnetic resonance imaging includes: defining (82) a first location (54) and a second location (56) on a surface representation; —generating (84) a line-structure of interest (60), —determining (86), for each location (62) of a plurality of locations (62), a normal direction (64); —determining (88) a mean normal direction (66); —determining (90) a mean imaging plane (68); —determining (92) a measure that is representative of angular deviations (43) of the determined normal directions (64); —based on the determined measure, determining (96) imaging planes (70); —determining (98) deviations of the determined normal directions (64) to the imaging planes (70); —acquiring (100) magnetic resonance images for all imaging planes (68, 70); and —determining (102) the wall thickness at a specific location (62) from the magnetic resonance image acquired in the imaging plane (70) that has the lowest angular deviation to the normal direction (64) at the specific location (62). A magnetic resonance imaging system (10) has a controller (26) configured to carry out steps (78-102) of the method. A
(Continued)

software module (50) carries out the method by implementing program code from a memory (28) and executed by a processor (30) of the magnetic resonance imaging system (10).

11 Claims, 5 Drawing Sheets

(51) Int. Cl.
    *A61B 5/055*     (2006.01)
    *A61B 5/107*     (2006.01)
    *G06T 7/62*     (2017.01)
    *G01R 33/54*     (2006.01)
    *G01R 33/56*     (2006.01)

(52) U.S. Cl.
    CPC .............. *A61B 5/1076* (2013.01); *G06T 7/62* (2017.01); *G01R 33/543* (2013.01); *G01R 33/5608* (2013.01); *G06T 2207/10088* (2013.01); *G06T 2207/20101* (2013.01); *G06T 2207/30048* (2013.01)

(56) References Cited

U.S. PATENT DOCUMENTS

| | | |
|---|---|---|
| 8,275,446 B2 | 9/2012 | Vining et al. |
| 2005/0099416 A1 | 5/2005 | Moreau-Gobard |
| 2008/0009709 A1 | 1/2008 | Guehring |
| 2010/0198072 A1 | 8/2010 | Abe et al. |
| 2011/0206260 A1 | 8/2011 | Bergmans |

OTHER PUBLICATIONS

Tobon-Gomez et al "3D Mesh Based Wall Thickness Measurement: Identification of Left Ventricular Hypertrophy Phenotypes" 2010 Annual International Conf. of the IEEE Enginerring in Med. and Bio Soc. Aug. 31-Sep. 4, 2010 p. 2642-2645.

Voigt et al "Atrial Wall Thickness Imaging for Cavotricuspid Isthmus Ablation" Proc. Intl. Soc. Mag. Reson. Med. 21 (2013) p. 0470.

Anselme F, Saoudi N, Poty H, Douillet R, Cribier A. Radiofrequency Catheter Ablation of Common Atrial Flutter Significance of Palpitations and Quality-of-Life Evaluation in Patients With Proven Isthmus Block. Circulation. 1999; 99:534-540.

Kajihara K, Nakano Y, Hirai Y, Ogi H, Oda N, Suenari K, Makita Y, Sairaku A, Tokuyama T, Motoda C, Fujiwara M, Watanabe Y, Kiguchi M, Kihara Y. Variable Procedural Strategies Adapted to Anatomical Characteristics in Catheter Ablation of the Cavotricuspid Isthmus Using a Preoperative Multidetector Computed Tomography Analysis. J. Cardiovasc. Electrophysiol. 2013;:n/a-n/a.

Koken P, Holthuizen R, Krueger S, Heese H, Weiss S, Smink J, Razavi R, Schaeffter T. Atrial Thickness Mapping for EP Ablation using Black-Blood Restricted Field of View MRI. In: Proceedings of the 19th Annual Meeting of ISMRM. Montreal, Canada: 2011. p. 3734.

Voigt T, Koken P, Harrison JE, Weiss S, Krueger S, Schaeffter T. Atrial wall thickness imaging for cavotricuspid isthmus ablation. In: Proceedings of the 21st Annual Meeting of ISMRM. Salt Lake City, USA: 2013. p. 470.

Frick M, Paetsch I, den Harder C, Kouwenhoven M, Heese H, Dries S, Schnackenburg B, de Kok W, Gebker R, Fleck E, Manka R, Jahnke C. Fully automatic geometry planning for cardiac MR imaging and reproducibility of functional cardiac parameters. J. Magn. Reson. Imaging. 2011; 34:457-467.

Heese H, Dries S, Bystrov D, Peters J, Ecabert O, den Harder C, de Kok W, van Muiswinkel AM. Consistency in automated versus manual definition of MRI scan volume orientations of the human heart. In: Proceedings of the 17th Annual Meeting of ISMRM. Honolulu, Hawaii, USA: 2009. p. 4681.

Hussain T, Clough RE, Cecelja M, Makowski M, Peel S, Chowienczyk P, Schaeffter T, Greil G, Botnar R. Zoom imaging for rapid aortic vessel wall imaging and cardiovascular risk assessment. J. Magn. Reson. Imaging. 2011; 34:279-285.

\* cited by examiner

METHOD OF SCAN GEOMETRY PLANNING FOR DETERMINING WALL THICKNESS OF AN ANATOMIC DETAIL USING MAGNETIC RESONANCE IMAGING

CROSS REFERENCE TO RELATED APPLICATIONS

This application is a U.S. national phase application of International Application No. PCT/EP2015/054798, filed on Mar. 9, 2015, which claims the benefit of EP Application Serial No. 14160641.8 filed on Mar. 19, 2014 and is incorporated herein by reference.

FIELD OF THE INVENTION

The invention pertains to a method for determining wall thickness of an anatomic detail, in particular the heart, of a human or animal subject of interest by magnetic resonance imaging, and a magnetic resonance imaging system being operated by employing such a method.

BACKGROUND OF THE INVENTION

There are several types of medical treatment, such as radiation therapy or radio frequency ablation that are known to benefit from an exact knowledge of the geometry of boundaries between different types of body tissue.

For instance, one of the most common forms of cardiac arrhythmias is atrial flutter (AFL). Radio frequency (RF) ablation has been shown as an effective treatment for patients with cardiac arrhythmia. Typical abnormal pathways of AFL include a re-entrant circuit around the tricuspid valve, crossing the cavotricuspid isthmus (CTI), which can be blocked by an ablation line created along the CTI. Since atrial wall thickness changes locally and is individual for each patient, the radio frequency ablation power used during clinical catheter ablation procedures has to be adjusted carefully to create transmural lesions, while avoiding wall perforation. Recently, it has been show that the outcome of isthmus ablation can be improved by taking anatomical characteristics such as wall thickness into consideration.

Further, magnetic resonance imaging is known to be able to provide information on anatomical characteristics such as wall thicknesses. In the paper by Koken, P. et al., "*Atrial Thickness Mapping for EP Ablation using Black-Blood Restricted Field of View MRI*", Proc. Intl. Soc. Mag. Reson. Med. 19 (2011), 3734, magnetic resonance-based atrial wall thickness imaging has been proposed for point-like measurements, employing a segmented 3D surface of the left atrium and a set of small, localized scans with high-resolution along the direction perpendicular to the atrial wall.

SUMMARY OF THE INVENTION

It is desirable to be able to determine a wall thickness of an anatomic detail, in particular of the heart, of a subject of interest in the most accurate way possible.

It is therefore an object of the invention to provide a method of determining wall thickness of an anatomic detail, in particular of the heart, of a subject of interest by magnetic resonance imaging.

The method comprises steps of
defining, on a surface representation of at least a portion of the anatomic detail, and based on operator input, at least a first location and a second location on the surface representation;
generating a line-structure of interest, wherein the line-structure comprises a plurality of locations on the surface representation, including the first location and the second location;
determining, for each location of the plurality of locations, a normal direction that is perpendicular to the surface of the anatomic detail at the location;
determining a mean normal direction from the determined normal directions of the plurality of locations;
determining a mean imaging plane being defined by the linear span of a vector having the mean normal direction and a vector that is arranged parallel to a straight line connecting the first location and the second location;
determining a measure that is representative of angular deviations of the determined normal directions of the plurality of locations from the mean imaging plane;
based on the determined measure, determining at least a second imaging plane, wherein the at least second imaging plane is generated by rotating the mean imaging plane about an axis given by the straight line connecting the first location and the second location;
determining the measure that is representative of angular deviations of the determined normal directions of the plurality of locations with regard to the second imaging plane;
acquiring magnetic resonance images for all imaging planes; and
determining the wall thickness at a specific location of the plurality of locations from the magnetic resonance image acquired in that imaging plane of the imaging planes that has the lowest angular deviation to the normal direction at the specific location.

The phrase "anatomic detail", as used in this application, shall particularly encompass but shall not be limiting to an organ, a gland or the bladder, or details of the vascular system like the vascular bifurcation, in particular arterial details, of the subject of interest.

The phrase "surface representation", as used in this application, shall particularly be understood as a 3D computer graphic of the anatomic detail. In the surface representation, the surface is preferably represented in a faceted mode, drawn as a series of planar regions like rectangles or triangles that approximates the surface of the anatomic detail. In general, in the surface representation the surface may be represented in any other mode that appears suitable to the one skilled in the art, for instance a wire frame representation.

The term "location", as used in this application, shall particularly be understood as one of a geometric center of a planar region, an edge of a planar region, and a vertex. In principle, by employing interpolation methods, a defined location may be any point of a planar region or of an edge, in case of a wire frame representation.

The term "line-structure", as used in this application, shall particularly be understood to comprise either a plurality of planar regions or a plurality of vertices of the surface representation, wherein each planar region of the planar regions or each vertex of the plurality of vertices is connected to another planar region of the planar regions or another vertex of the plurality of vertices. In this way, the line-structure of interest usually has a specified width.

The phrase "mean normal direction", as used in this application, shall particularly be representable by a vector whose components are averages of components of vectors representing the determined normal directions in the same coordinate system. A vector representing a determined normal direction can be assigned to a basis point of the location on the surface representation. The vector representing the mean normal direction can be assigned to a location obtained from averaged coordinates of the locations of the plurality of locations. All vectors, including the vector representing the mean normal direction, may preferably be normalized to have unit length.

One advantage of the method lies in that wall thickness of the anatomic detail along the line-structure having varying normal directions can be determined without errors due to partial volume effects, which reduces systematic measurement errors.

Another advantage of the method lies in that the high in-plane resolution inherent to magnetic resonance imaging can be utilized to the benefit of precisely determining wall thickness of the anatomic detail.

The magnetic resonance images may preferably be acquired using a ZOOM imaging technique, known in the art (e.g. Hussain, T. et al. "*Zoom imaging for rapid aortic vessel wall imaging and cardiovascular risk assessment*", J. Magn. Reson. Imaging. 2011, 34: 279-2859 as a spin echo-based technique with high spatial resolution that differs from traditional spin echo imaging in that the 180° refocusing radio frequency pulse is applied perpendicular to the 90° excitation pulse, which limits the field of view to the intersection of these pulses.

In a preferred embodiment, the method further comprises a step of automatically generating the line-structure of interest, based on the defined at least first location and the second location on the surface representation. By that, the line-structure of interest can readily be defined, without being prone to human subjectivity or error.

If the line-structure of interest is a geodesic on the surface representation, a coarse pre-adjustment for arranging the imaging planes can be accomplished.

Preferably, the first location and the second location are arranged in end regions of the line-structure of interest or even mark ends of the line-structure of interest. The term "end region", as used in this application, shall particularly be understood as a region of the line-structure that encompasses one of the ends and a subsequent third of a length of the line-structure.

The surface representation of at least a portion of the anatomic detail employed by the disclosed method may have been generated from an image acquired by an image modality other than the magnetic resonance imaging system, for instance by a computer tomography (CT) system. The CT image data may have a data format that is compatible with a DICOM (Digital Imaging and Communication in Medicine) standard and may be stored in a Picture Archiving and Communication System (PACS). DICOM standard is equivalent to ISO standard 12052:2006 "*Health informatics—Digital imaging and communication in medicine (DICOM) including workflow and data management*". The magnetic resonance imaging system may have access to the PACS to be able to extract the CT image and may be configured to generate a surface representation by itself. Alternatively, the PACS may provide the option to extract a surface representation from the stored CT image data.

In another preferred embodiment, the method further includes a step of applying a model-based automatic image segmentation technique to a three-dimensional magnetic resonance scan of at least the portion of the anatomic detail to determine the surface representation of at least the portion of the anatomic detail. In this way, an in-situ surface representation of the anatomic detail of the subject of interest can be provided without the need and effort for alignment of an actual position a subject of interest with the surface representation.

In yet another embodiment of the method, the measure that is representative of the angular deviation of a specific determined normal direction is an angle by which the mean imaging plane has to be rotated about the axis in order to make the specific determined normal direction closest to be lying in the mean imaging plane. In this way, angular deviations of the determined normal directions from the mean imaging plane can readily be quantified.

In one embodiment, as the line-structure of interest may have a specified width, the mean imaging plane may be shifted by an affine transformation, in particular a translation, prior to being rotated about the axis, toward one of the edges for making the specific determined normal direction closer to be lying in the mean imaging plane. In this way, an improved determination of the angular deviation of a specific determined normal direction from the imaging planes can be accomplished.

In another preferred embodiment, the method further comprises steps of
calculating a measure of variation of the determined measures that are representative of the angular deviations of the determined normal directions of the plurality of locations from the mean imaging plane; and
determining a plurality of imaging planes, wherein each imaging plane is generated by rotating the mean imaging plane about the axis, and is positioned in an angular section defined by an angular interval around the angular position of the mean imaging plane, wherein a size of the angular interval is based on the calculated measure of variation, and wherein the plurality of imaging planes includes the at least second imaging plane.

In this way, it can be readily ensured that an imaging plane is provided such that its angular deviation to the normal direction at the specific location fulfills a specified precision requirement.

Preferably, the measure of variation may be the standard deviation, in its commonly used definition, of the determined measures that are representative of the angular deviations. Alternatively, the measure of variation may be given by the sum of absolute differences of the angular deviations of the determined normal directions from the mean imaging plane. Further measures of variation that appear suitable to the one skilled in the art may also be employed.

In one embodiment, the step of determining the plurality of imaging planes comprises arranging the imaging planes of the plurality of imaging planes in the angular interval in angular positions such that adjacent imaging planes, including the mean imaging plane, are separated by an identical angular step. In this way, a range of the angular deviations of the determined normal directions of the plurality of locations from the mean imaging plane can readily be covered.

Preferably, the size of the identical angular step may be determined from the calculated measure of variation.

In yet another preferred embodiment, the method further comprises steps of
separating the second imaging plane from the mean imaging plane by a predetermined angular step in a first rotating direction;
if a range of the determined measure that is representative of angular deviations exceeds the predetermined angular step, determining at least a third imaging plane, wherein the third imaging plane is generated by rotating the mean imaging plane about the axis, in a rotating direction that is opposite to the first rotating direction, to an angular position such that adjacent imaging planes, including the mean imaging plane, are separated by the predetermined angular step, and the mean imaging plane is arranged between the second imaging plane and the third imaging plane;

determining a next imaging plane that is generated by rotating the mean imaging plane about the axis in the first rotating direction to an angular position in which it is separated to the next adjacent imaging plane by the predetermined angular step, if at least one determined measure is outside an angular interval defined by a maximum angular difference of the imaging planes with regard to the axis; and repeating the preceding step, with rotating the mean imaging plane about the axis in alternating rotation directions, until the range of the determined measure that is representative of angular deviations falls below a size of the angular interval with regard to the axis.

In this way, the range of the determined measure that is representative of the angular deviations can be covered by a minimum number of imaging planes, while at the same time precision requirements can be met that may be implicitly given by the predetermined angular step.

In a further aspect of the invention, a magnetic resonance imaging system configured for acquiring magnetic resonance images of at least a portion of a subject of interest is provided. The magnetic resonance imaging system comprises:

an examination space provided to position at least the portion of the subject of interest within, a main magnet configured for generating a static magnetic field $B_0$ in the examination space, a magnetic gradient coil system configured for generating gradient magnetic fields superimposed to the static magnetic field $B_0$, at least one radio frequency antenna device that is configured for applying a radio frequency excitation field $B_1$ to nuclei of or within the portion of the subject of interest for magnetic resonance excitation, at least one radio frequency antenna device that is configured for receiving magnetic resonance signals from the nuclei of or within the portion of the subject of interest that have been excited by applying the radio frequency excitation field $B_1$, a control unit configured for controlling functions of the magnetic resonance imaging system, and a signal processing unit configured for processing magnetic resonance signals to determine magnetic of at least the portion of the subject of interest from the received magnetic resonance signals.

The control unit is configured to carry out steps of an embodiment of any of the methods disclosed herein or a combination thereof.

In one embodiment, the control unit is connectable to an electrocardiography device and/or to a respiration monitoring device. By employing output signals of these devices for triggering, magnetic resonance images can be acquired at a desired status of heart activity and/or respiration of the subject of interest.

In yet another aspect of the present invention, a software module is provided for carrying out an embodiment of any of the methods disclosed above or a combination thereof, of determining wall thickness of an anatomic detail of a subject of interest. The method steps to be conducted are converted into a program code of the software module, wherein the program code is implementable in a memory unit of the magnetic resonance imaging system and is executable by a processor unit of the magnetic resonance imaging system. The processor unit may be the processor unit of the control unit that is customary for controlling functions of a magnetic resonance imaging system. The processor unit may, alternatively or supplementary, be another processor unit that is especially assigned to execute at least some of the method steps.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
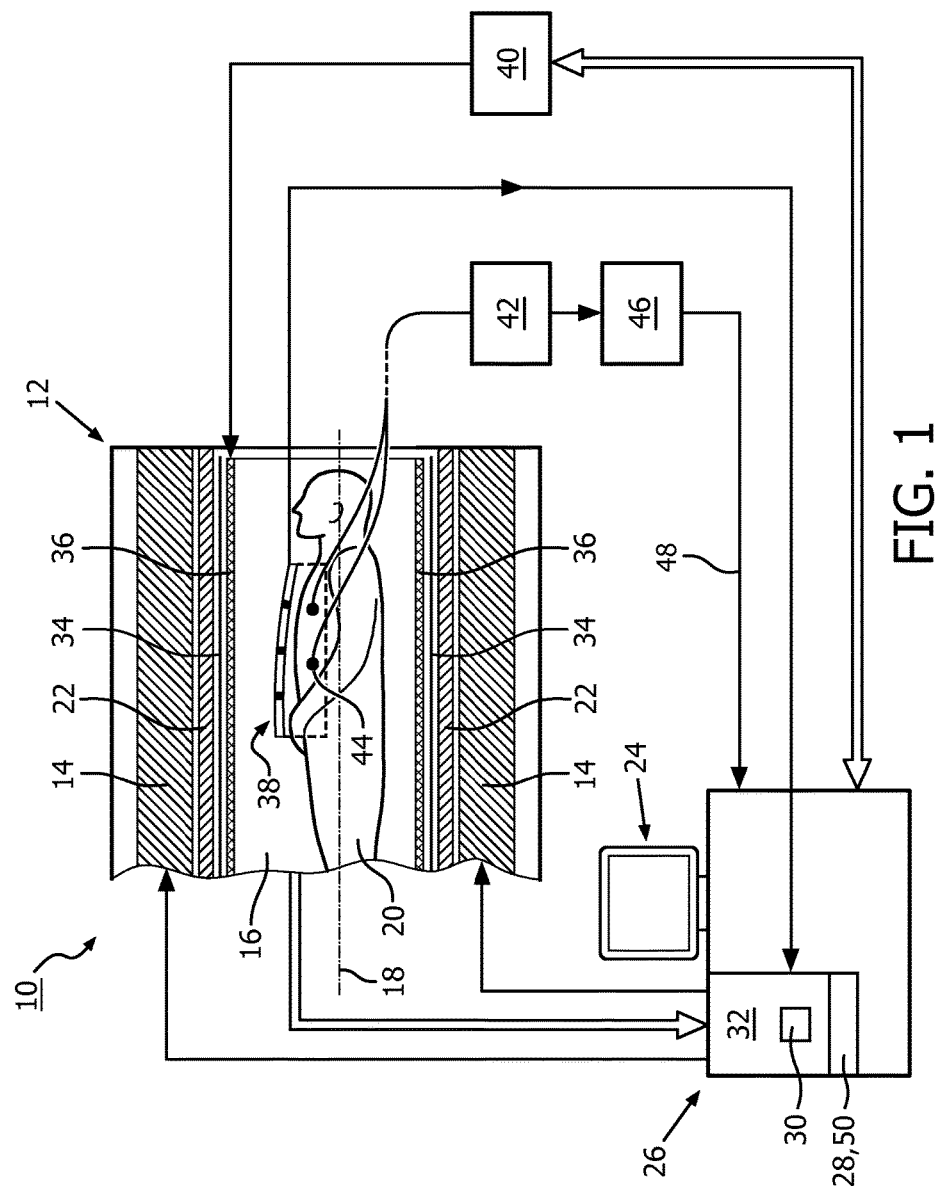
FIG. 1 shows a schematic illustration of a part of an embodiment of a magnetic resonance imaging system in accordance with the invention.

FIG. 1 shows a schematic illustration of a part of an embodiment of a magnetic resonance imaging system 10 configured for acquiring magnetic resonance images of at least a portion of a subject of interest 20, usually a patient. The magnetic resonance imaging system 10 comprises a scanning unit 12 having a main magnet 14. The main magnet 14 has a central bore that provides an examination space 16 around a center axis 18 for the subject of interest 20 to be positioned within, and is further provided for generating a static magnetic field $B_0$ at least in the examination space 16. For clarity reasons, a customary table for supporting the subject of interest 20 has been omitted in FIG. 1. The static magnetic field $B_0$ defines an axial direction of the examination space 16, aligned in parallel to the center axis 18. It is appreciated that the invention is also applicable to any other type of magnetic resonance imaging systems providing an examination region within a static magnetic field.

Further, the magnetic resonance imaging system 10 comprises a magnetic gradient coil system 22 configured for generating gradient magnetic fields superimposed to the static magnetic field $B_0$. The magnetic gradient coil system 22 is concentrically arranged within the bore of the main magnet 14.

The magnetic resonance imaging system 10 comprises a control unit 26 configured to control functions of the magnetic resonance imaging system 10. The control unit 26 includes a human interface device 24 including a monitor unit having a touch-sensitive screen.

Furthermore, the magnetic resonance imaging system 10 includes a radio frequency antenna device 36 designed as a whole-body coil that is provided for applying a radio frequency excitation field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter 40 to the whole-body coil. The whole-body coil has a center axis and, in the operational state, is arranged concentrically within the bore of the main magnet 14 such that the center axis of the whole-body coil and the center axis 18 of the scanning unit 12 coincide. As is well known in the art, a cylindrical metal radio frequency shield 34 is arranged concentrically between the magnetic gradient coil system 22 and the whole-body coil.

Moreover, the magnetic resonance imaging system 10 comprises a plurality of radio frequency antenna devices 38 provided for receiving magnetic resonance signals from the nuclei of or within the subject of interest 20 that have been excited by applying the radio frequency excitation field $B_1$. The radio frequency antenna devices of the plurality of radio frequency antenna devices 38 are designed as an array of local coils that are intended to be positioned proximal to a region of the subject of interest 20 to be imaged, namely the heart. The local coils are configured for receiving magnetic resonance signals from the excited nuclei of or within the portion of the subject of interest 20 to be imaged during radio frequency receiving time periods which are distinct from the radio frequency transmit time periods.

Furthermore, the magnetic resonance imaging system 10 comprises a signal processing unit 32 configured for processing magnetic resonance signals to determine magnetic resonance images of at least the portion of the subject of interest 20 from the received magnetic resonance signals. Moreover, the signal processing unit 32 is furnished with a segmentation software module known in the art for carrying out automated image segmentation.

For the acquisition of magnetic resonance images of the heart of the subject of interest 20, the magnetic resonance imaging system 10 is further equipped with an electrocardiogram device 42 and a synchronization unit 46.

The electrocardiogram device 42 is provided for taking measurements of the electrocardiogram data of the heart of the subject of interest 20. To this end, a plurality of electrodes 44 of the electrocardiogram device 42 may be arranged at the subject of interest 20, for instance according to an orthogonal lead set. Further, the electrocardiogram device 42 includes means for filtering the electrocardiogram data to reduce artifacts generated by magnetic gradient fields. Suitable filtering means are known to the person skilled in the art and shall therefore not be described in more detail herein.

The electrocardiogram device 42 is coupled to the synchronization unit 46, which in turn is coupled to the control unit 26. The control unit 26 is configured to be synchronized by trigger signals 48 that are provided by the synchronization unit 46, upon detecting the prominent R-wave of the QRS-complex of the electrocardiogram signal, for a generation of control signals for the magnetic gradient coil system 22 to generate gradient magnetic fields. To this end, the control unit 26 is configured to generate a plurality of sequences upon receiving the trigger signals 48, each sequence comprising radio frequency fields and magnetic gradient fields.

The magnetic resonance imaging system 10 may additionally comprise a respiration monitoring device (not shown in FIG. 1). The respiration monitoring device may be configured to provide the control unit 26 with an output signal whose level represents a respiration state of the subject of interest 20. The output signal may be displayed on the monitor unit of the human interface device 24. In this way, a breathing pattern and, in particular, breath-hold periods of the subject of interest 20 may be checked by an operator.

In the following, an embodiment of a method of determining wall thickness of an anatomic detail, namely the atrium wall thickness of the heart, of the subject of interest 20 is described. A principal flow chart of the method is given in FIG. 2. Although described in an application to determine heart wall thickness, it is noted that the method is also applicable to other anatomic details of the subject of interest 20. In preparation of operating the magnetic resonance imaging system 10, it shall be understood that all involved units and devices are in an operational state and configured as illustrated in FIG. 1.

In order to be able to carry out the method as a specific operation of the magnetic resonance imaging system 10, the control unit 26 comprises a software module 50 (FIG. 1). The method steps to be conducted are converted into a program code of the software module 50, wherein the program code is implementable in a memory unit 28 of the control unit 26 and is executable by a processor unit 30 of the control unit 26.

Figure 2:
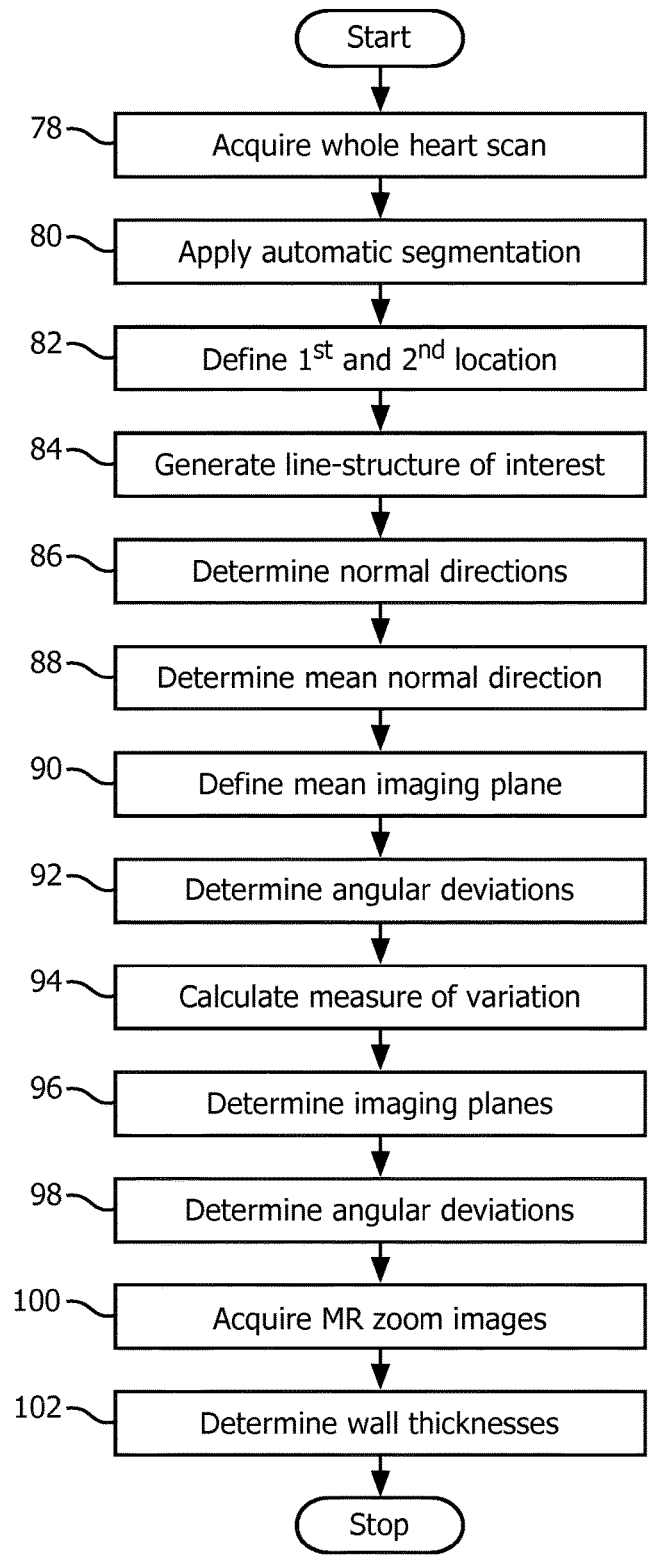
FIG. 2 is a flowchart of an embodiment of a method in accordance with the invention, of operating the magnetic resonance imaging system pursuant to FIG. 1.

In a preparatory step 78 of the method illustrated in FIG. 2, an ECG-triggered and respiratory-navigated 3D balanced steady-state free precession (bSSFP) magnetic resonance scan of the whole heart is acquired.

Figure 3:
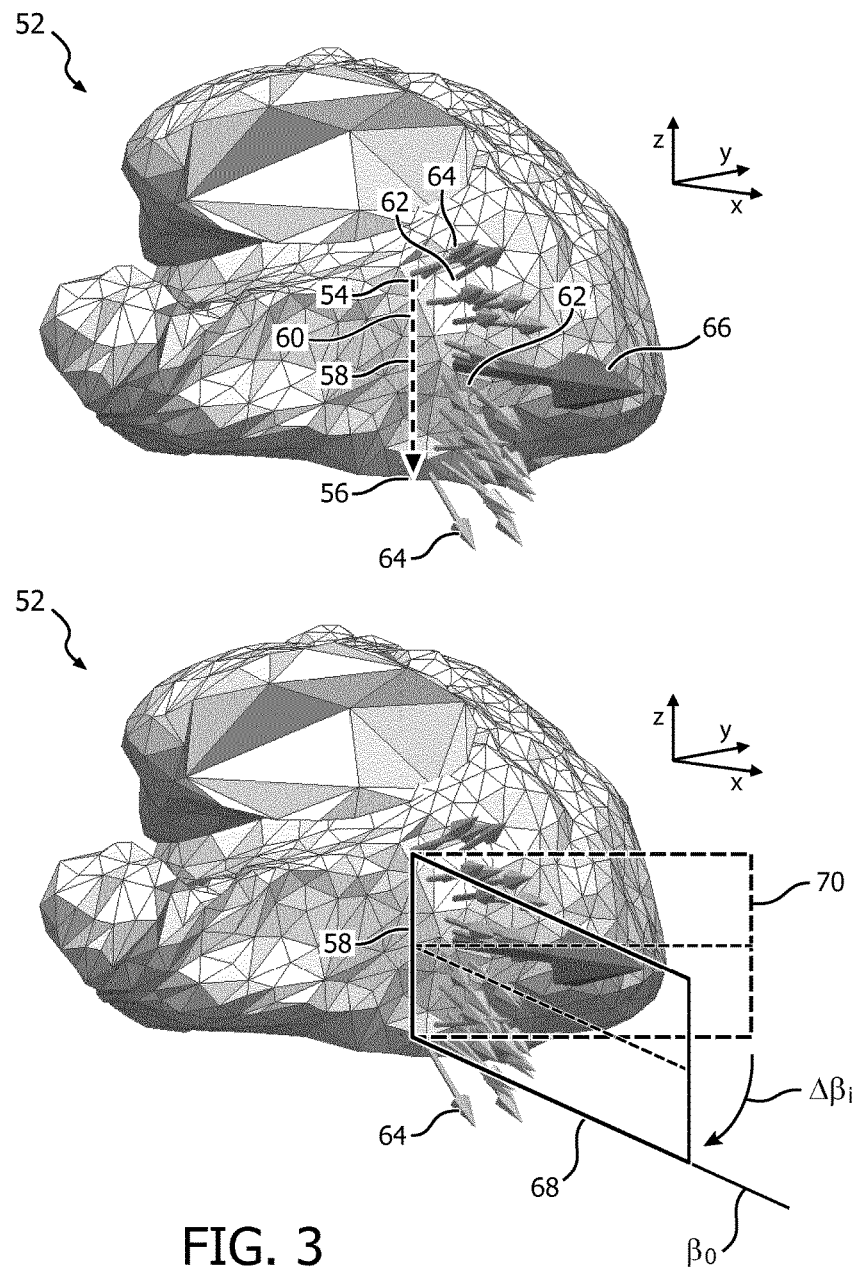
FIG. 3 illustrates steps of the method pursuant to FIG. 2 carried out at a surface representation of the right atrium of the heart of the subject of interest.

In a next step 80 of the method, a model-based automatic image segmentation technique is applied to the 3D scan data of the whole heart by the signal processing unit 32 for determining a surface representation of the different heart chambers. The surface representation of the right atrium 52 is illustrated in FIG. 3. The surface of the right atrium 52 is approximated by a series of planar regions designed as triangular facets.

Then, in another step 82, both the surface and the reformatted 3D dataset are used to manually define, based on operator input via the human interface device 24, a first location 54 and a second location 56 on the surface representation to define a line-structure of interest 60. The line-structure of interest 60 is automatically generated in a next step 84, based on the defined first location 54 and the second location 56 of the surface representation, as a geodesic having a path length s on the surface representation.

The first location 54 on the surface representation is proximal to the tricuspid valve (TV), and the second location 56 of the surface representation is proximal to the inferior vena cava (IVC). The geodesic on the surface representation between the first location 54 and the second location 56 generates the line-structure of interest 60 that is understood to approximate the cavotricuspid isthmus (CTI). The line-structure of interest 60 includes the first location 54 and the second location 56.

As is illustrated in FIG. 3, the line-structure of interest 60 comprises a plurality of locations 62 on the surface representation, given by geometric centers of the triangular facets, and has a specified width of two triangular facets in a direction perpendicular to the geodesic. For reasons of clarity, only two locations 62 of the plurality of locations 62 are exemplarily marked by a reference numeral.

In a further step 86 of the method, for each location 62 of the plurality of locations 62 of the line-structure of interest 60, a normal direction 64 is determined that is perpendicular to the surface of the right atrium 52 at the location 62. The normal direction 64 of a specific location 62 is represented by a vector of unit length assigned to the geometric center of the specific location 62 as a basis point. Again, for reasons of clarity only two numbers directions 64 are marked by a reference numeral.

Then, a mean normal direction 66 is determined from the determined normal directions 64 of the plurality of locations 62 in a next step 88. The vector representing the mean normal direction 66, although having unit length, is shown enlarged in FIG. 3 for illustration purposes.

In the following step 90, a mean imaging plane 68 is determined that is defined by the linear span of the vector representing the mean normal direction 66 and a vector that is arranged parallel to a straight line connecting the first location 54 and the second location 56. It is understood that the straight line connecting the first location 54 and the second location 56 is not embedded in the surface representation but is a straight line in the three-dimensional space, and does not necessarily have to have more points in common with the surface representation than the first location 54 and the second location 56.

Then, in the next step 92 of the method, a measure is determined as follows that is representative of angular deviations $\Delta\beta_i$, of the determined normal directions 64 of the plurality of locations 62 from an angular position $\beta_0$ of the mean imaging plane 68 with regard to an axis 58 of rotation provided by the straight line.

Figure 4:
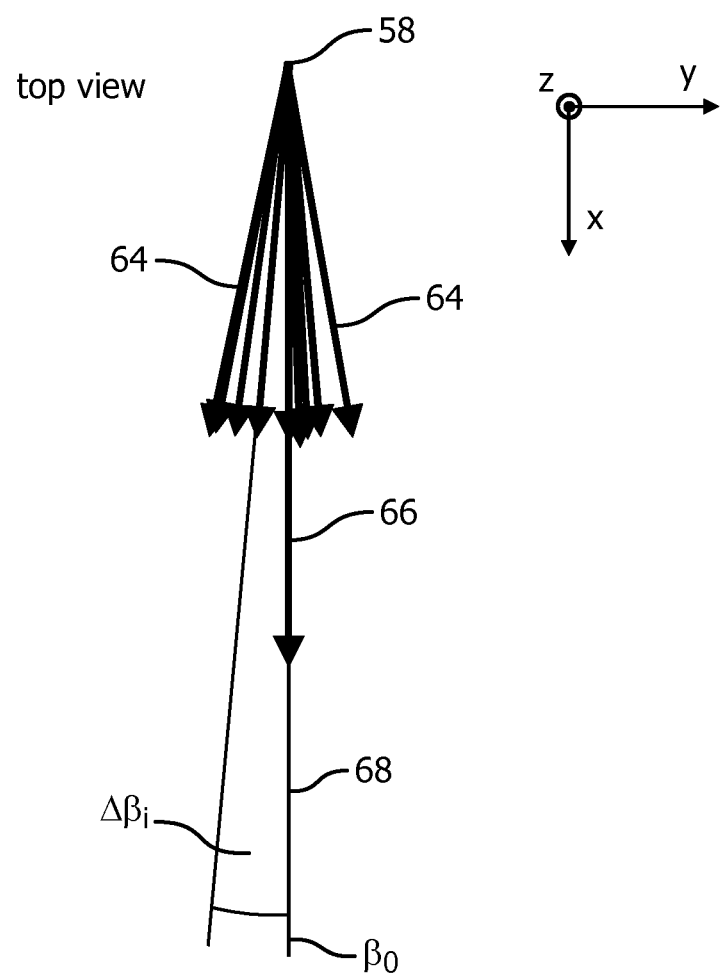
FIG. 4 is an illustration of determining a measure that is representative of angular deviations of determined normal directions from a mean imaging plane as a step of the method pursuant to FIG. 2.

With no loss of generality, a coordinate system can be chosen such that the vector representing the mean normal direction 66 is aligned with the x-axis (FIG. 4) of the coordinate system, and thus only has an x-component that is different from zero. Because the vector is of unit length, the x-component is equal to one. The vectors representing the normal directions 64 at the locations 62 have components $(x_i, y_i, z_i)$ that are generally different from zero in the chosen coordinate system. The measure that is representative of angular deviations $\Delta\beta_i$ of the determined normal directions 64 from the mean imaging plane 68 is obtained from the vector dot product of the vector representing the normal direction 64 at the location 62 and the vector representing the mean normal direction 66. The vector dot product result is then given by the x-component of the vector representing the normal direction 64 at the location 62.

In a next step 94, from the determined measures that are representative of the angular deviations $\Delta\beta_i$ defined as $$\Delta\beta_i := \beta_i - \beta_0$$

($\beta_i$: angular position of determined normal direction 64 having index i with regard to axis 58 of rotation) of the determined normal directions 64 of the plurality of locations 62 from the mean imaging plane 68, a measure of variation is calculated that is given as the standard deviation $\sigma$ in its commonly used definition $$\left[ \sum_i (\beta_i - \beta_0^2)/(n-1) \right]^{1/2},$$

i=1, 2, ..., n).

Figure 5:
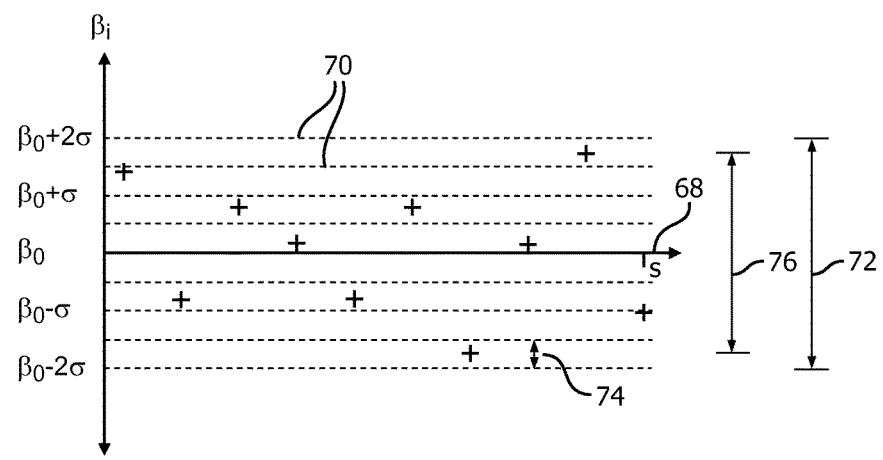
FIG. 5 shows a measure representative of angular deviations of determined normal directions from the mean imaging plane and magnetic resonance imaging planes determined in accordance with an embodiment of the method of the invention.

In the next step 96 of the method, based on the determined measure representative of the angular deviations $\Delta\beta_i$ of the determined normal directions 64, a plurality of eight imaging planes 70 is determined, wherein each imaging plane 70 of the plurality of imaging planes 70 is generated by rotating the mean imaging plane 68 about the axis 58 of rotation (FIG. 5). The plurality of imaging planes 70 is positioned in an angular section defined by an angular interval 72 around the angular position $\beta_0$ of the mean imaging plane 68. The angular interval 72 is based on the calculated measure of variation, has a size of 4σ and is symmetrically arranged on either side of the angular position $\beta_0$ of the mean imaging plane 68.

The step 96 of determining the plurality of imaging planes 70 comprises arranging the imaging planes 70 of the plurality of eight imaging planes 70 in the angular interval 72 in angular positions such that adjacent imaging planes 70, including the mean imaging plane 68, are separated by an identical angular step 74 of σ/2 (FIG. 5). The angular positions of the imaging planes 70 are indicated in FIG. 5 by horizontal dashed lines.

Then, in the following step 98 of the method, the same measure that is representative of angular deviations of the determined normal directions 64 of the plurality of locations 42 is determined but with regard to each imaging plane 70 of the plurality of imaging planes 70.

The measure that is representative of the angular deviation of a specific determined normal direction 64 from a specific imaging plane 70 can be considered to be an angle by which the specific imaging plane 70 has to be rotated about the axis 58 in order to make the specific determined normal direction 64 closest to be lying in the rotated specific imaging plane 70. Optionally, this can be combined with applying a translational transformation to the specific determined normal direction 64.

In a further step 100 of the method, magnetic resonance images are acquired for all imaging planes 70 of the plurality of imaging planes 70, including the mean imaging plane 68. The magnetic resonance images are acquired employing a black blood turbo spin echo (TSE) pulse sequence with fat suppression and zoom imaging.

In a final step 102 then, for all locations 62 along the path length s of the line-structure of interest 60, the wall thickness at a specific location 62 of the plurality of locations 62 is determined from the magnetic resonance image acquired in that imaging plane 70 of the imaging planes 70 that has the lowest angular deviation to the normal direction 64 at the specific location 62. To this end, an automatic approach to determine the wall thickness is implemented. Signal intensity profiles are determined along a direction that is perpendicular to a line connecting the first location 54 and the second location 56 as shown in the acquired magnetic resonance zoom image. The wall thickness is defined to be twice the standard deviation of a Gaussian fit to the intensity profile.

Figure 6:
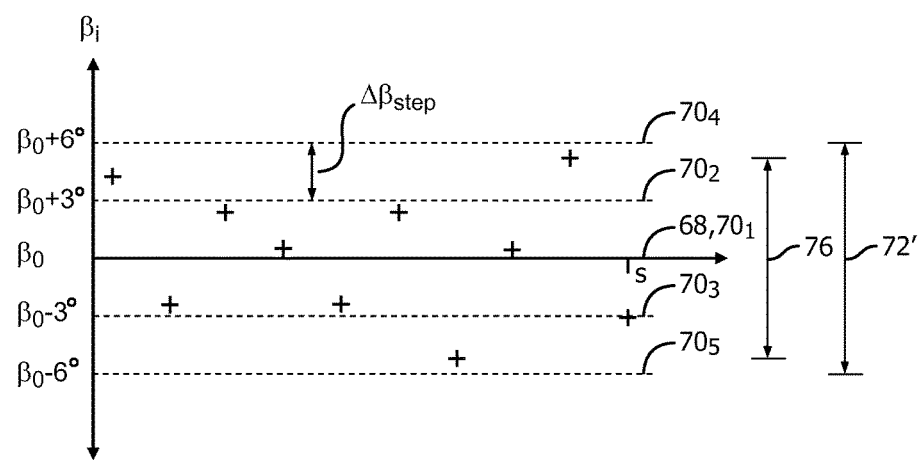
FIG. 6 shows the measure representative of the angular deviations of determined normal directions from the mean imaging plane and magnetic resonance imaging planes determined in accordance with another embodiment of the method of the invention.

In an alternative embodiment of the method (FIG. 6), after determining the measure that is representative of angular deviations $\Delta\beta_i$ of the determined normal directions 64 of the plurality of locations 62 from the mean imaging plane 68, a second imaging plane $70_2$ is generated by rotating the mean imaging plane 68 about the axis 58 and separating the second imaging plane $70_2$ from the mean imaging plane 68 by a predetermined angular step $\Delta\beta_{step}$ in a first rotating direction. In this embodiment, the predetermined angular step $\Delta\beta_{step}$ has a size of 3°. The predetermined angular step $\Delta\beta_{step}$ may be derived from requirements of a maximum tolerable error of wall thickness determination for an expected wall thickness of the anatomic detail.

Because the angular range 76 of the determined measure that is representative of angular deviations $\Delta\beta_i$ exceeds the predetermined angular step $\Delta\beta_{step}$, a third imaging plane $70_3$ is determined in a next step, wherein the third imaging plane $70_3$ is generated by rotating the mean imaging plane 68 about the axis 58, in a rotating direction that is opposite to the first rotating direction (indicated by a negative sign in FIG. 6), to an angular position such that adjacent imaging planes $70_{k-1}$, $70_k$ (k≥1), including the mean imaging plane 68 which in this context is identified as imaging plane $70_1$, are separated by the predetermined angular step $\Delta\beta_{step}$, so that the mean imaging plane 68 is arranged between the second imaging plane $70_2$ and the third imaging plane $70_3$.

Then, if at least one determined measure falls outside an angular interval 72' defined by a maximum angular difference of the imaging planes $70_k$ with regard to the axis 58, a next imaging plane $70_{k+1}$ is determined that is generated by rotating the mean imaging plane 68 about the axis 58 in the first rotating direction to an angular position in which it is separated to the next adjacent imaging plane $70_k$ by the predetermined angular step $\Delta\beta_{step}$.

The preceding step is repeated, by rotating the mean imaging plane 68 about the axis 58 in alternating rotation directions, until the angular range 76 of the determined measure that is representative of angular deviations $\Delta\beta_i$ falls below a size of the angular interval 72' with regard to the axis 58.

After acquiring magnetic resonance images by employing a black blood turbo spin echo (TSE) pulse sequence with fat suppression and zoom imaging, for all locations 62 of the line-structure of interest 60, the wall thickness at a specific location 62 of the plurality of locations 62 is determined from the magnetic resonance image acquired in that imaging plane 70 of the imaging planes 70 that has the lowest angular deviation to the normal direction 64 at the specific location 62, in the same way as described for the early embodiment.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST

| | |
|---|---|
| 10 | magnetic resonance imaging system |
| 12 | scanning unit |
| 14 | main magnet |
| 16 | examination space |
| 18 | center axis |
| 20 | subject of interest |
| 22 | magnetic gradient coil system |
| 24 | human interface device |
| 26 | control unit |
| 28 | memory unit |
| 30 | processor unit |
| 32 | signal processing unit |
| 34 | radio frequency shield |
| 36 | radio frequency antenna device (transmitting) |
| 38 | plurality of radio frequency antenna device (receiving) |
| 40 | radio frequency transmitter |
| 42 | electrocardiogram device |
| 44 | electrode |
| 46 | synchronization unit |
| 48 | trigger signal |
| 50 | software module |
| 52 | right atrium |
| 54 | first location |
| 56 | second location |
| 58 | axis |
| 60 | line-structure of interest |
| 62 | location |
| 64 | normal direction |
| 66 | mean normal direction |
| 68 | mean imaging plane |
| 70 | imaging plane |
| 72 | angular interval |
| 74 | angular step |
| 76 | range of angular deviations |
| 78 | step of acquiring heart scan |
| 80 | step of applying segmentation |
| 82 | step of defining $1^{st}$ and $2^{nd}$ locations |
| 84 | step of generating line-structure |
| 86 | step of determining normal directions |
| 88 | step of determining mean normal direction |
| 90 | step of defining mean image plane |
| 92 | step of determining angular deviations |
| 94 | step of calculating measure of variation |
| 96 | step of determining imaging planes |
| 98 | step of determining angular deviations |
| 100 | step of acquiring MR images |
| 102 | step of determining wall thicknesses along line-structure |
| $B_0$ | static magnetic field |
| $B_1$ | radio frequency excitation field |
| $\beta_0$ | angular position of mean imaging plane |
| $\Delta\beta_i$ | angular deviation of normal direction from mean direction |
| $\Delta\beta_{step}$ | predetermined angular step |
| s | path length along line-structure |

The invention claimed is:

1. A method for determining wall thickness of an anatomic detail of a subject of interest by magnetic resonance imaging, the method comprising steps of defining, on a surface representation of at least a portion of the anatomic detail, and based on operator input, at least a first location and a second location on the surface representation;

generating a line-structure of interest, wherein the line-structure comprises a plurality of locations on the surface representation, including the first location and the second location;

determining, for each location of the plurality of locations, a normal direction that is perpendicular to the surface of the anatomic detail at the location;

determining a mean normal direction from the determined normal directions of the plurality of locations;

determining a mean imaging plane being defined by the linear span of a vector having the mean normal direction and a vector that is arranged parallel to a straight line connecting the first location and the second location;

determining a measure that is representative of angular deviations (Dbi) of the determined normal directions of the plurality of locations from the mean imaging plane;

based on the determined measure, determining at least a second imaging plane, wherein the at least second imaging plane is generated by rotating the mean imaging plane about an axis given by the straight line connecting the first location and the second location;

determining the measure that is representative of angular deviations of the determined normal directions of the plurality of locations with regard to the second imaging plane;

acquiring magnetic resonance images for all imaging planes; and determining the wall thickness at a specific location of the plurality of locations from the magnetic resonance image acquired in that imaging plane of the imaging planes that has the lowest angular deviation to the normal direction at the specific location.

2. The method as claimed in claim 1, further comprising automatically generating the line-structure of interest, based on the defined at least first location and the second location on the surface representation.

3. The method as claimed in claim 1, wherein the line-structure of interest is a geodesic on the surface representation.

4. The method as claimed in claim 1 further comprising applying a model-based automatic image segmentation technique to a three-dimensional magnetic resonance scan of at least the portion of the anatomic detail to determine the surface representation of at least the portion of the anatomic detail.

5. The method as claimed in claim 1, wherein the measure that is representative of the angular deviation (Dbi) of a specific determined normal direction is an angle by which the mean imaging plane is rotated about the axis in order to make the specific determined normal direction closest to be lying in the mean imaging plane.

6. The method as claimed in claim 1 further comprising calculating a measure of variation(s) of the determined measures that are representative of the angular deviations (Dbi) of the determined normal directions of the plurality of locations from the mean imaging plane; and determining a plurality of imaging planes, wherein each imaging plane is generated by rotating the mean imaging plane about the axis, and is positioned in an angular section defined by an angular interval around the angular position (b0) of the mean imaging plane, wherein a size of the angular interval is based on the calculated measure of variation(s), and wherein the plurality of imaging planes includes the at least second imaging plane.

7. The method as claimed in claim 6, wherein the step of determining the plurality of imaging planes comprises arranging the imaging planes of the plurality of imaging planes in the angular interval in angular positions such that adjacent imaging planes, including the mean imaging plane, are separated by an identical angular step.

8. The method as claimed in claim 1, further comprising:

separating the second imaging plane from the mean imaging plane by a predetermined angular step in a first rotating direction;

if a range of the determined measure that is representative of angular deviations exceeds the predetermined angular step, determining at least a third imaging plane, wherein the third imaging plane is generated by rotating the mean imaging plane about the axis, in a rotating direction that is opposite to the first rotating direction, to an angular position such that adjacent imaging planes, including the mean imaging plane, are separated by the predetermined angular step, and the mean imaging plane is arranged between the second imaging plane and the third imaging plane;

determining a next imaging plane that is generated by rotating the mean imaging plane about the axis in the first rotating direction to an angular position in which it is separated to the next adjacent imaging plane by the predetermined angular step, if at least one of the determined measures is outside an angular interval defined by a maximum angular difference of the imaging planes with regard to the axis; and repeating the preceding step, with rotating the mean imaging plane about the axis in alternating rotation directions, until the range of the determined measure that is representative of angular deviations falls below a size of the angular interval with regard to the axis.

9. A magnetic resonance imaging system configured for acquiring magnetic resonance images of at least a portion of a subject of interest, comprising:

an examination space provided to position at least the portion of the subject of interest within;

a main magnet configured for generating a static magnetic field $B_0$ in the examination space;

a magnetic gradient coil system configured for generating gradient magnetic fields superimposed to the static magnetic field $B_0$;

at least one radio frequency antenna device that is configured for applying a radio frequency excitation field $B_1$ to nuclei of or within the portion of the subject of interest for magnetic resonance excitation;

at least one radio frequency antenna device that is configured for receiving magnetic resonance signals from the nuclei of or within the portion of the subject of interest that have been excited by applying the radio frequency excitation field $B_1$;

a control unit configured for controlling functions of the magnetic resonance imaging system; and a signal processing unit configured for processing magnetic resonance signals to determine magnetic resonance images of at least the portion of the subject of interest from the received magnetic resonance signals;

wherein the control unit is configured to carry out the method set forth in claim 1.

10. A software module for carrying out the method as set forth in claim 1 of determining wall thickness of an anatomic detail of a subject of interest by magnetic resonance imaging, wherein the method steps to be conducted are converted into a program code of the software module, wherein the program code is implementable in a memory unit of the magnetic resonance imaging system and is executable by a processor unit of the magnetic resonance imaging system.

11. A magnetic resonance imaging system configured for acquiring magnetic resonance images of at least a portion of a subject of interest, the system comprising:

a magnetic resonance scanner including:

a main magnet configured for generating a static magnetic field $B_0$ in an examination space, the examination space being configured to receive at least a portion of a subject therein, a magnetic gradient coil system configured for generating gradient magnetic fields superimposed to the static magnetic field $B_0$, at least one radio frequency antenna device configured for applying a radio frequency excitation field $B_1$ to nuclei of or within the portion of the subject for magnetic resonance excitation and for receiving magnetic resonance signals from the nuclei of or within the portion of the subject of interest that have been excited by applying the radio frequency excitation field $B_1$;

at least one processor configured for:
controlling the magnetic gradient coil system and the at least one radio frequency antenna device to induce magnetic resonance within the portion of the subject,
reconstructing magnetic resonance images form the magnetic resonance signals received by the at least one radio frequency antenna device,
controlling a display device to display the magnetic resonance images, the magnetic resonance images including surface images and slice images,
receiving from an operator input at least a first location and a second location on a selected surface image,
segmenting at least a portion of the selected surface image to generate a segmented surface representation including a plurality of locations, each location having a plurality of vertices and a surface normal, the surface normal of each location being perpendicular to a surface of the location,
generating a line-structure of interest including a plurality of contiguous locations on the segmented surface representation, including the first location and the second location,
determining the surface normal for each location of the plurality of locations of the line-structure,
determining a mean normal direction from the determined surface normals of the plurality of locations of the line-structure,
determining a mean imaging plane, the mean imaging plane being defined by a linear span of a first vector having the mean normal direction and a second vector that is arranged parallel to a straight line connecting the first location and the second location,
determining angular deviations (Dbi) between the surface normal of the plurality of locations of the line-structure from the mean imaging plane,
based on the determined angular deviations, determining at least a second imaging plane, wherein the at least second imaging plane is generated by rotating the mean imaging plane about an axis given by the straight line connecting the first location and the second location,
determining angular deviations of the surface normals of the plurality of locations of the line-structure with regard to the second imaging plane,
acquiring magnetic resonance images for all imaging planes, and
determining a wall thickness at a specific location of the plurality of locations of the line-structure from a one of the magnetic resonance slice images acquired in a one of the imaging planes that has a lowest angular deviation to the surface normal of the specific location.

* * * * *